United States Patent [19]

List et al.

[11] 4,340,752

[45] Jul. 20, 1982

[54] PROCESS FOR THE PURIFICATION OF TEREPHTHALIC ACID

[75] Inventors: Ferdinand List, Marl; Friedrich-August Orlowski, Haltern, both of Fed. Rep. of Germany

[73] Assignee: Chemische Werke Hüls AG, Marl, Fed. Rep. of Germany

[21] Appl. No.: 888,612

[22] Filed: Mar. 21, 1978

[30] Foreign Application Priority Data

Apr. 4, 1977 [DE] Fed. Rep. of Germany ....... 2714985

[51] Int. Cl.$^3$ .............................................. C07C 51/42
[52] U.S. Cl. ....................................... 562/485; 562/486
[58] Field of Search ................. 260/525; 562/485, 486

[56] References Cited

U.S. PATENT DOCUMENTS 3,431,296  3/1969  Ichikawa et al. .................. 260/525
3,887,612  6/1975  Shigeyasu et al. .................. 260/525

Primary Examiner—Alan Siegel
Attorney, Agent, or Firm—Wells & Wells

[57] ABSTRACT

A process for the purification of terephthalic acid in which a dispersion of the terephthalic acid in a liquid dispersant such as acetic acid is continuously pumped repeatedly through a cycle. Fresh dispersion is fed continuously into the cycle while simultaneously a corresponding amount of treated dispersion is removed. The cycle comprises a heater and a cooler and the cooler serves as a crystallizer. The dispersion prior to entering the heater is subjected to a highly effective particle comminution and is exposed upstream of or in the heater to an oxygen containing gas such as air. The acetic acid dispersant is removed from the treated dispersion and recycled to the cycle.

13 Claims, 1 Drawing Figure

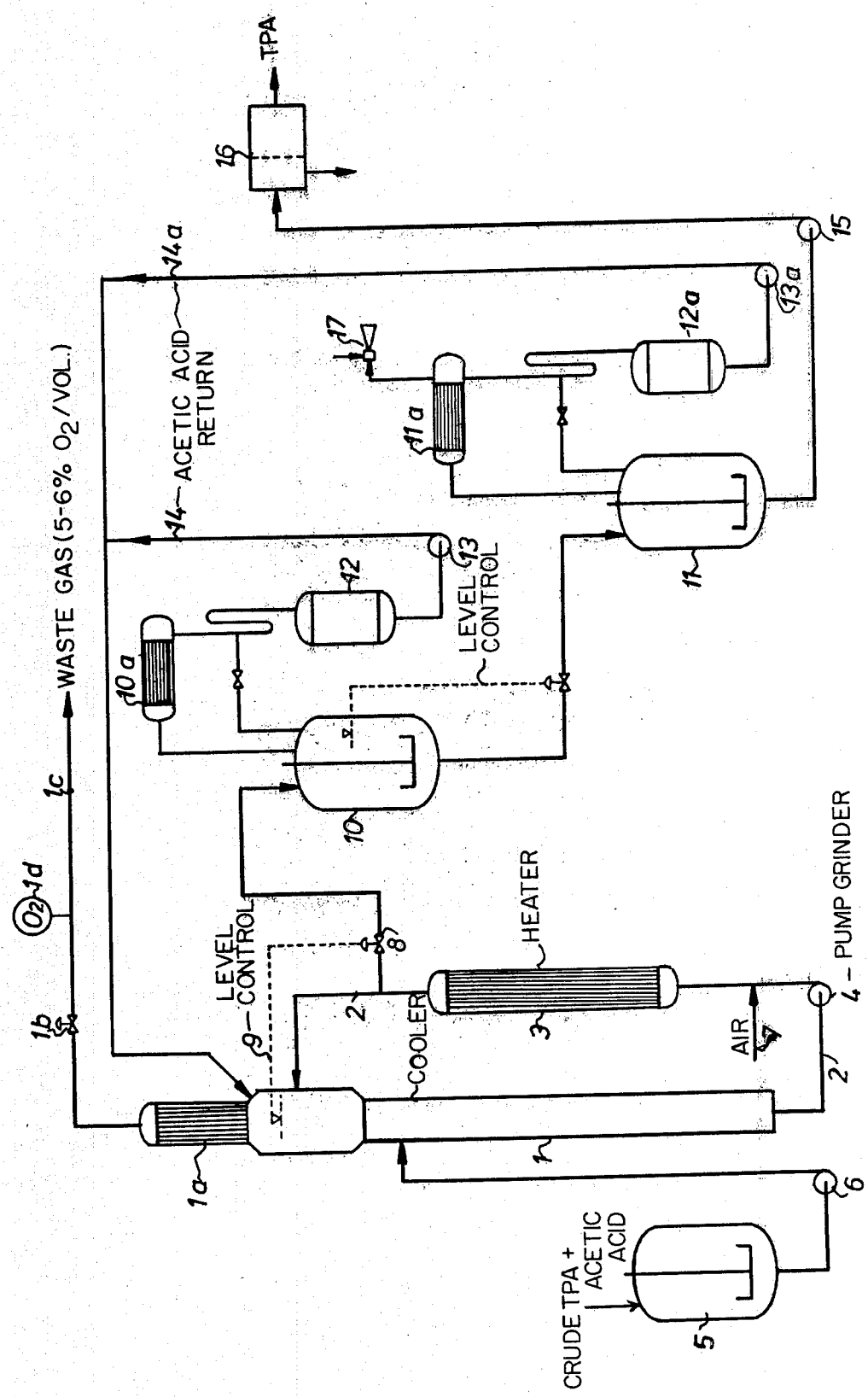

PROCESS FOR THE PURIFICATION OF TEREPHTHALIC ACID

CROSS REFERENCES TO RELATED APPLICATIONS

Applicants claim priority under 35 USC 119 for application P 27 14 985.3 filed Apr. 4, 1977 in the Federal Republic of Germany.

The disclosure of copending application Ser. No. 704,955 of Ferdinand List et al filed July 13, 1976 and corresponding to British Patent No. 1,237,786 is incorporated herein to show the state of the art of liquid phase air oxidation processes for making phthalic acids and the crude therephthalic acid containing terephthalaldehydic acid starting materials of the present invention.

BACKGROUND OF THE INVENTION

The field of the present invention is processes for purifying terephthalic acid.

The state of the art of methods for purifying terephthalic acid may be ascertained by reference to U.S. Pat. Nos. 3,660,478; 3,859,344 and 3,887,612 and British Pat. Nos. 982,629; 1,237,786 and 1,454,478, the disclosures of which are incorporated herein.

As is known, a particularly pure terephthalic acid (TPA) is required for the production of fibers, sheets, films, or also injection-molding compositions of polyesters of terephthalic acid, for example of polyethylene terephthalate, in order to obtain the desired film- and fiber-forming properties, high melting points, pronounced crystallinity, and complete absence of color.

Crude TPA as obtained, for example, in accordance with the conventional oxidation process for p-xylene in acetic acid on heavy metal ions and bromine ions with the use of air, is, however, contaminated generally by oxidation intermediates, such as p-toluic acid and terephthalaldehydic acid (TPAA), as well as by catalyst salts. While the catalyst residues and p-toluic acid can be readily removed by leaching with warm acetic acid, the TPAA resists such a treatment. Since TPA is hardly at all soluble in solvents and melts only at above 425° C. under decomposition, the customary purifying methods, such as, for example, recrystallization or distillation, cannot be readily employed. However, the TPAA can be present in the TPA up to an extent of 3–5% and causes the polyester to assume a deeply dark coloring, and furthermore lowers the melting point and crystallinity of the polyester considerably.

For this reason, various purifying processes have been suggested for TPA, and among these also methods employing a secondary oxidation.

In accordance with British Pat. No. 982,629 crude TPA is to be subjected to a secondary oxidation step in acetic acid at 250° C.; in this process, the TPAA contained in the solid TPA particles is dissolved and can be oxidized. However, this method is uneconomical, because at above 200° C. the acetic acid is degraded by oxidation, on the one hand, and the installations are corroded, on the other hand. The process cannot be operated usefully, though, at below 200° C., because the solubility of the TPA is too low; a purified TPA is obtained in this case only if the crude TPA has already a very high degree of purity.

In conformance with the above, British Pat. No. 1,454,478 teaches that a purifying effect is achieved by way of the secondary oxidation of a TPA slurry in acetic acid at 190°–195° C. with air only if the first oxidation stage has left only a small amount of TPAA in the TPA; however, to attain this objective, a long oxidation period is required at a high temperature (for example 175 minutes at 210° C.), and the required time period can only be shortened somewhat by further increasing the temperature or the degree of dilution. The purifying effect, though, is only 66%, even under optimum conditions.

Quite similarly, U.S. Pat. No. 3,859,344 discloses that a crude TPA containing 570 p.p.m. of TPAA can be purified to 370–290 p.p.m. TPAA by subjecting the crude TPA to a secondary oxidation and a residence time in several crystallizers. The purifying effect is, accordingly, only 35–48% and here again there is the prerequisite that the crude acid be already relatively pure.

U.S. Pat. No. 3,887,612 seeks to overcome these disadvantages by recommending a pumping and agitating treatment instead of the secondary oxidation. In this process, the crude TPA is made into a slurry with acetic acid, recirculated for about 3 hours by means of a pump, which reduces the particle size of the TPA by 10–30%, heated to 130°–180° C., and separated. The most advantageous example, however, shows a purification of the TPA of only from 90 p.p.m. to 30 p.p.m. TPAA. The reference conveys the further teaching that a comminution of the TPA particles of more than 30% is to be avoided, since the impurities are concentrated in the close proximity to the surface of the particles; consequently, the pumping and agitating process has the purpose of moderately abrading the surfaces. In contrast thereto, if the particles are reduced by, for example, 60%, then too many particles are produced having a very large surface area in total, which perforce adsorb the TPAA dissolved in the acetic acid. Here again, therefore, the process has limitations in that the concentration of TPAA in the dispersant determines the concentration of the TPAA in the TPA separated from this dispersant. Thus, this process also requires a crude TPA which is already pure.

U.S. Pat. No. 3,660,478 proceeds along still another path by proposing to circulate the slurry of crude TPA in acetic acid through a crystallizing loop at least ten times alternatingly in a temperature interval of 0.5–17° C. and to withdraw a small portion for processing, the heat being removed by evaporative cooling. Per each cycle, 1–10% of the dissolved proportion of TPA is to be recrystallized. The reference sets forth a degree of purity of up to 90%; however, since the starting material is to be crude acid containing up to 5% TPAA and p-toluic acid, the degree of efficiency of the proposed process is entirely unsatisfactory.

SUMMARY OF THE INVENTION

Therefore, in spite of all of these suggestions, there is still an urgent need for a method making it possible to purify crude TPA, independently of the degree of contamination so that a pure TPA is obtained which meets all requirements.

According to the present invention crude TPA starting material having a TPAA concentration of about 0.5 to 5 percent by weight, especially 1 to 3 percent by weight, or about 10,000 to 30,000 p.p.m. is dispersed in acetic acid in a weight ratio of TPA to acetic acid of 5:95 to 60:40 The dispersion of TPA and acetic acid is circulated continuously in cycle comprising a comminuting pump, a heater and a cooler which serves as a crystallizer with exposure to an oxygen containing gas upstream of or in the heater. Fresh dispersion is added continuously to the cycle while simultaneously a corresponding amount of treated dispersion is removed.

In a particular embodiment, acetic acid is removed from the treated dispersion and recycled to the cycle.

The TPAA concentration in the dried TPA final product is about 0.07 to 0.01 percent by weight, especially 0.06 to 0.02 percent by weight or about 600 to 200 p.p.m.

TPA is added to the cycle continuously at a rate of about 15 to 150 kilograms of TPA per hour and the cycle is circulated at a rate of about 1500 to 30,000 liters per hour. The average number of cycles carried out through the comminuting pump, heater and cooler is about 5 and 100.

The temperature range in the cycle is about 180° to 210° C. while the temperature range in the heater is about 195° to 210° C. and in the cooler is about 180° to 195° C.

During the course of the treatment cycle the TPA particles are comminuted by about 50 to 90% of their average diameter. The average diameter of the TPA particles in the crude dispersion starting material is about 10 to 150 microns while the TPA particles in the treated dispersion are about 5 to 10 microns.

Air is introduced into the cycle at the rate of about 150 to 1500 liters per hour and the percent by volume of oxygen in the waste gas from the cycle is about 1 to 4.

The amount of acetic acid recycled per hour ranges from about 50 to 500 liters per hour and comprises about 50 to 500 percent by weight of the acetic acid introduced as feed dispersion into the cycle.

BRIEF DESCRIPTION OF THE DRAWING

The drawing illustrates the mode of operation of this invention as follows

Crude TPA from the catalytic air oxidation of p-xylene in an acetic acid solution is mixed, after centrifuging, in the agitator vessel 5 with acetic acid. This cold dispersion is continuously introduced via pump 6 into the tower-like cooler 1 equipped with a reflux condenser 1a, a pressure-maintaining valve 1b, and a waste gas conduit 1c with oxygen meter 1d and having a capacity of 200 liters. Via the lateral bypass line 2, the cooler 1 is in communication with a heater 3 having a capacity of 7 m² and heated with high-pressure steam, this heater having the effect of a dissolving stage, the cooler and heater thus forming a cycle. In the lower part of the lateral bypass line is an inclineddisk grinding pump 4 (of the type of a "Gorator" by Hoelscher-Technik, Herne). The dispersion conveyed by means of this grinding pump first flows through the heater 3 and then returns into the upper part of the cooler 1, namely above the feed point for the fresh, colder dispersion. The intermixing of the recirculated, hot dispersion with the cold, fresh dispersion results in a direct cooling effect triggering a recrystallization of the TPA. The acetic acid evaporating in the upper part of the cooler 1 is condensed in the reflux condenser 1a, flows back, and effects an additional cooling action. On the pressure side of the inclined-disk grinding pump 4, air is introduced into the system via conduit 7. Above the heater 3, hot suspension is continuously withdrawn via a pneumatically operated conical-seat valve 8. The amount thus withdrawn is dimensioned so that the filling level in the cooler 1 remains constant; the radioactive level meter 9 controls the discharge pulses.

The thus-discharged, hot dispersion enters a multistage evaporative crystallizing unit. The evaporative cooling stages consist respectively of one agitated vessel 10, 11 with tubular heat exchangers 10a and 11a attached thereto, wherein the evaporating acetic acid is condensed. During this step, the pressure pertaining to the condensation temperature is obtained in the agitated vessel, i.e. in the cooling stage (1) (agitator 10), for example, a pressure of 2–3 bar is obtained at a temperature of 150° C. In the cooling stage (2) (agitator 11), a temperature of, for example 50° C. is maintained by evaporating the acetic acid under reduced pressure, e.g. about 70–80 millibar. The liquid volumes in the agitated vessels 10 and 11 are selected so that with a continuous mode of operation the residence times of the solution to be cooled are sufficient for crystallization. The vacuum is produced by means of the ejector 17, operated by steam or acetic acid vapor.

The acetic acid obtained in the receivers 12, 12a of the two evaporative cooling stages can be either returned or fed with the aid of piston metering pumps 13, 13a via conduits 14, 14a into the purifying stage proper, so that a higher dilution and thus an increase in the amount of dissolved TPA is attained within the cycle 1, 2, 3, 4. The discharge, cooled to 50° C. (stirrer 11) is introduced via an eccentric-screw pump 15 into the liquid-solid separating stage 16 which can consist, for example, of a centrifuge, a filter, a suction cell filter, a strip cell filter, or a solid-jacket centrifuge. The thus-separated TPA is subjected to a secondary washing step with acetic acid and dried.

DESCRIPTION OF THE PREFERRED EMBODIMENTS

A TPA starting material suitable for the process is one which contains interfering proportions of TPAA; especially suitable is a TPA obtainable according to one of the conventional oxidation processes, especially in the oxidation of p-xylene with atmospheric oxygen in acetic acid and in the presence of heavy metal compounds, such as cobalt acetate or manganese acetate, optionally in the further presence of ketones or bromine compounds.

Basically, there is no upper limit for the TPAA content in this crude TPA; this differentiates the process of the present invention from the conventional methods. The proportion of TPAA can be, for example, advantageously 0.5–5% weight, especially 1–3% weight. The process is not impaired, either, by the fact that the TPA starting material contains still other oxidation intermediates as contamination, for example p-toluic acid. Thus, a very well usable TPA is one obtained in the oxidation of 100 parts of p-xylene in 420 parts of acetic acid in the presence of 3.3 parts of cobalt acetate and 1.7 parts of potassium bromine at 180° C. with air while maintaining a constant excess of air in the waste gas, corresponding to 2–4% by volume of excess oxygen and with a mean residence time of 60 minutes, in accordance with British Pat. No. 1,237,786, Example 1, which TPA consists of:

97.05% by weight of TPA
2.42% by weight of TPAA
0.43% by weight of p-toluic acid
0.1% by weight of benzoic acid.

The crude TPA, frequently obtained in the presence of acetic acid, can be used in the centrifuged condition, moist with acetic acid, optionally washed with pure acetic acid.

The TPA is purified in the disperse form. Suitable liquid dispersants are all liquids wherein TPA is soluble in marked quantities at an elevated temperature, particularly lower carboxylic acids, such as propionic acid or butyric acid, but above all acetic acid. The acetic acid can also contain up to 10% water. Furthermore suitable as dispersants are the solvents employed in the catalytic air oxidation of p-xylene, e.g. lactones (gamma-butyrolactone, alpha-valerolactone) nitriles (benzonitrile, chloro- and nitrobenzonitrile, aliphatic nitriles such as acetonitrile), ketones, such as methyl ethyl ketone, and aldehydes, such as acetaldehyde.

The dispersions can contain the proportion of solids within wide limits but must fulfill various conditions: They are to be capable of being circulated by pumping, they must not form sediments in pipelines, they must offer the introduced oxygen an oxidizing effect, and they must finally permit a highly efficient comminution of the TPA particles. According to experience, those dispersions are suitable wherein the proportion of solids is 5-60%, above all 10-50%, especially 20-40%.

The dispersion is pumped through a cycle containing a heater as well as a cooler, which latter serves as the crystallizer.

The heater can be designed in a variety of ways, but must meet the condition that the dispersion does not settle therein and that the TPA particles are brought in close contact with the previously introduced, oxygen-containing gas. Upright heat exchangers have proven to be particularly well suitable, for example tubular heat exchangers and pipe coil heat exchangers, which are suitably heated by means of high-pressure steam or thermal oil.

Also the cooler which serves as the crystallizer can be constructed as desired. An upright, tower-like design has proven to be especially advantageous; this construction can be equipped with jacket cooler, but preferably exhibits a reflux condenser as the cooler, which is set on top of the structure. An additional cooling effect can be attained by introducing into the cooler a fresh dispersion having a temperature lower than that of the recirculated dispersion, preferably 10°-150° C., especially 15°-50° C.

The continuous mode of operation entails that the fresh dispersion, especially if it is used as a direct coolant, is especially advantageously introduced into the cycle continuously and, accordingly, the same amount of the treated dispersion is continuously discharged; this is done most suitably between the heater and the cooler.

The thus-fed and thus-discharged proportion of the dispersion determines, under otherwise identical circulation conditions (total quantity introduced into the cycle and pump efficiency), the average residence time in the cycle as well as the average number of cycles and thus of the treatments of this invention.

The average number of cycles is to be 5-100, preferably 20-80, especially 30-50. It can clearly be seen that a lower number of cycles will be sufficient if the degree of contamination of the crude TPA is low, if the particle comminution is especially thorough, if the particle concentration in the dispersion is low, if the amount of oxygen available is high, if the temperature level in the upper zone is high, if the temperature difference in the cycle is considerable and/or if oxidation catalysts are present; conversely, a higher number of cycles will be selected if a strongly contaminated TPA is treated in a more concentrated dispersion under less efficient particle comminution at a lower temperature and a lower temperature difference without oxidation catalysts and/or with less oxygen.

Accordingly, about 5-80% by volume, preferably 10-40% by volume, especially 15-35% by volume of fresh dispersion can be added, based on the filling volume of the cycle, and the same amount of treated dispersion can be withdrawn. These numerical values, depending on the operating conditions, can be exceeded, or the values used can be less, and they can also be shifted with respect to their optimum range.

Advantageously, the process of this invention is carried out at an elevated temperature, preferably in a range from 150° to 220° C., especially from 180° to 210° C., in order to ensure an adequate oxidation velocity and a favorable crystallizing process.

The temperature difference between the outlets of the heater and of the cooler is to be 0.5°-20° C., preferably 1°-15° C., especially 2°-6° C. In general, a higher difference of, for example, 10°-15° C. is chosen if the degree of contamination of the crude TPA and/or the proportion of solids in the suspension is increased, and a lower temperature difference of, for example, 2° C., is selected at correspondingly lower values.

According to the invention, the dispersion is subjected, prior to its entrance into the heater, to a highly efficient particle comminution. Such a comminution is understood to mean a mechanical shattering of the TPA crystals. This shattering has the effect that the occluded TPAA contaminations are uncovered and are immediately converted into the desired TPA during the subsequent oxidizing step under heating, without giving the thus-liberated TPAA an opportunity to be readsorbed on the TPA particles or to be even reincorporated into the growing TPA crystals during the cooling and crystallization processes which follow within the cycle.

Accordingly, suitable for the particle comminuting step is any type of ball mill, hammer mill, pin beater mill, disk-type impact pulverizer mill, colloid mill, rolling mill, oscillating mill, jet mill, screen mill, serrated-disk mill, Hollander, roller frame, toothed colloidal mill, trigonal toothed rotary mill, capable of dividing the TPA particles.

A grinding efficiency is desirable, by means of which the particles are comminuted during the course of the treatment by 20-95%, preferably 50-90%, of their average diameter, i.e. at least partially to colloidal fineness (see, in this connection, "Ullmanns Enzyklopaedie der technischen Chemie" [Ullmann's Encyclopedia of Technical Chemistry] 3rd edition [1951], 1:620). It can be seen that these numerical values can be exceeded either in the upper or lower directions, if the crystallizing effect, due to the choice of the temperature difference, the residence times, and/or the degree of dilution of the dispersion in the cycle by recycling the solvent from the evaporative crystallization, is especially high or particularly low; furthermore, the desired efficiency is dependent on the degree of contamination and on the initial particle size of the crude TPA, and on the effect intended.

The comminuting device is arranged upstream or downstream of the pump which maintains the dispersion in circulation. Suitable pumps are rotary pumps of a known construction, eccentric-screw pumps, axial-flow pumps, etc. The circulation can also be accomplished in accordance with the principle of the mammoth pump or by thermosiphon effect. However, preferably a pump is employed which also effects the comminution in addition to its conveying and mixing function. Suitable, for example, is an inclined-disk grinding pump which has a rapidly revolving, circular or elliptical rotor disk which is obliquely arranged on the shaft. This disk is serrated along its outer edge, the serrations fitting with narrow tolerances into the counter serrations arranged in the housing. This pump generates axially and radially superimposed flow movements of a very high turbulence and effects an extremely powerful mechanical comminution of the TPA particles.

It is also possible to use a trigonal toothed rotary mill for a simultaneously highly effective comminution in conjunction with a strong conveying effect. In this trigonal toothed rotary mill, the comminution is accomplished by shear stress between the tooth flanks of rotor and stator, which have alternating depths, wherein up to three grinding stages can be combined within one machine.

During or after the comminuting step, optionally before entrance into the heater, the dispersion is exposed to an oxygen-containing gas, for example air, or oxygen-enriched air. This gas is advantageously introduced via customary feeding systems effecting a satisfactory distribution of the gas in the liquid stream, such as, for example, fixed porous plates, nozzles, or movable installations which distribute the gas thoroughly in the liquid via correspondingly arranged outlet openings. In a particularly simple and effective way, the gas can be introduced directly into the grinding zone of the inclined-disk grinding pump or of the trigonal toothed rotary mill, thus obtaining an extremely fine distribution of the gas bubbles in the liquid. If desired, the gas can also be introduced into the lower part of the heater.

The liquid-phase oxidation of TPAA is enhanced by increasing the $O_2$ concentration. Since the reaction mixture does not contain any p-xylene, the $O_2$ content in the waste gas can rise up to 13% by volume with a pressure in the system of 12 bar, without attaining the explosion limit of acetic acid-air. The oxygen-containing gas is, therefore, dimensioned so that there is an oxygen excess of 30-55%, especially 40-50%, based on the liberated TPAA.

If desired, it is also possible to feed to the cycle a suitable oxidation catalyst in incremental portions or in a continuous manner, for example cobalt acetate, potassium bromide, manganese acetate. This holds true, in particular, when using a TPA which has been freed of the catalyst salts stemming from the preceding p-xylene oxidation stage by means of an acetic acid washing step performed beforehand. In contrast thereto, if the TPA separated by centrifuging from the p-xylene oxidation stage, which contains a residual moisture of about 8-20%, is utilized directly, i.e. without an additional acetic acid washing step, then the amount of catalyst entrained with the adhering mother liquor is in any event more than enough for the desired secondary oxidation of the TPAA. A content of bound cobalt of 10-150 p.p.m., especially 30-100 p.p.m., and a content of bound bromine of 30-160 p.p.m., especially 50-120 p.p.m., in each case based on the bulk of the total dispersion, has proven to be advantageous in the cycle. The catalyst mixture, suitably dissolved in the dispersant, is introduced into the cycle via a metering pump, e.g. a piston or diaphragm metering pump, in the zone of the air feed. Of course, it is also possible to premix the fresh dispersion with a suitable amount of catalyst mixture and to maintain the required catalyst level by feeding fresh dispersion into the cycle.

The process of this invention, as compared to the above-mentioned modes of operation, exhibits a number of advantages in principle. Although the process is conducted at relatively low temperatures, the claimed process makes it possible, even with the use of a crude TPA having a very high TPAA content (>20,000 p.p.m.), to lower the TPAA concentration by more than 99%. This, however, means that the crude TPA can stem from a process wherein p-xylene has been oxidized at very gentle temperatures, e.g. 180°-190° C., and simultaneously at very high throughput rates. Since the process of this invention proper operates likewise at relatively moderate temperatures, preferably below 200° C., losses in material are avoided which otherwise occur due to thermal and oxidative degradation, and there is no necessity for overcoming additional corrosion problems.

In spite of these relatively gentle operating conditions, the TPAA content in the discharged acetic acid is still below the limits of analytical detection (below 0.003%). This is also the reason for the fact that the very finely ground TPA grain, in spite of its extremely large surface area, cannot reabsorb any dissolved TPAA. For the same reason, it is also possible to reintroduce the acetic acid obtained in receivers 12 and 12a as a condensate directly into the cycle, since during the concentration of the suspension carried out in conjunction therewith in the agitator vessels 10 and 11 there is no danger of crystallizing TPAA. This provides simultaneously an additional cooling effect and a higher degree of dilution, and thus an increase in the amount of dissolved TPA, which is equivalent to an increase in the purifying effect, thus attained without the use of additional amounts of solvent. At the same time, with a concentration of the cooled dispersion, the subsequent separation of solids (e.g. by centrifuging, filtration) is considerably facilitated.

COMPARATIVE EXAMPLES

1. Simple Extraction

A crude TPA produced by the catalytic air oxidation of p-xylene in an acetic acid solution in the presence of cobalt acetate, hydrogen bromide, and potassium bromide at a temperature of 180°-190° C. and under a pressure of 10-12 bar has a TPAA content of 2.42%; furthermore, this crude TPA contains 250 p.p.m. of potassium salts and 85 p.p.m. of cobalt salts.

This TPA is mixed in an agitated flask with reflux condenser and heating bath with acetic acid in a weight ratio of 1:3 and is then heated under high-speed agitation (1,500 r.p.m.) to 118° C. The thus-extracted TPA is vacuum-filtered, washed with fresh acetic acid in a weight ratio of 1:1, and dried. While the metallic salts (Co=4 p.p.m., K=5 p.p.m.) present in the crude acid can be removed by a simple washing step with hot acetic acid, the TPAA content can only be lowered to an insignificant amount even by many hours of extraction with boiling acetic acid:

| Extraction Time Hours | % TPAA in Extracted and Dried TPA |
| --- | --- |
| 9 | 1.88 |
| 20 | 1.64 |
| 36 | 1.64 |

2. Cycle with Comminution without Oxidation

Crude TPA as in Comparative Example 1 is utilized in a cycle with a working-up process conducted in accordance with the illustration, but without the air feed means 7.

At room temperature, a suspension of TPA and acetic acid in a weight ratio of 1:3 is produced in the agitated vessel 5, and this suspension is fed via pump 6 into the cooler 1 until the cycle 1, 2, 3, 4 is filled up, which is the case after a feed of about 300 liters. The suspension is circulated with the aid of the inclined-disk grinding pump 4. The pump operates at 1,500 r.p.m., corresponding to a circulating power of 9,000 l./h. At the same time, the suspension is heated by the heater, operated with high-pressure steam, until a temperature of 210° C. and a pressure of 10–11 bar have been attained. This is the case after about 30 minutes. After the suspension has been circulated for about 120 minutes at a temperature of 210° C. (above 3), 150 kg. of dispersion, corresponding to 37.5 kg. of TPA and 112.5 kg. of acetic acid, is fed continuously per hour into the cycle 1, 2, 3, 4 from the agitated vessel 5 via pump 6. During this step, a temperature of 206° C. is obtained in the crystallizing zone 1 below the feed of the fresh dispersion, whereas the temperature in the dissolving zone above the heat exchanger is unchanged at 210° C. By way of the pneumatically operated conical-seat valve 8, the circulating, hot dispersion is continuously discharged into the two-stage evaporative crystallization unit 10, 11, wherein the discharge pulses are controlled by the radioactive level meter 9. In the cooling stage (agitator 10), a temperature of 150° C. is obtained under a pressure of 2–3 bar by evaporation of the acetic acid which is precipitated in the attached tubular heat exchanger 10a and flows back into the agitator 10; the residence time of the suspension in this agitator is about 1–2 hours. In the second cooling stage (agitator 11), a temperature of 50° C. is accordingly obtained under a reduced pressure of 80 millibar. The residence time in this cooling stage is about 2–3 hours. From there, the suspension, cooled to 50° C., is introduced via pump 15 into the solid-jacket centrifuge 16. The separated TPA is washed, to remove the adhering mother liquor, with acetic acid (weight ratio of TPA: HAc = 1:0.6), and then dried.

The dry TPA has the following TPAA contents:
4,200—4,100—4,800—4,000 p.p.m.

whereas in the liquid discharge from the separating stage, TPAA concentrations are present of:
6,500—6,600—6,000—5,800 p.p.m.

The ash content of the washed and dried acid is ≦10 p.p.m. (Co = <1 p.p.m.; K = 2 p.p.m.). The calculated estimate shows that the TPAA balance evolves, i.e. the TPAA dissolved out of the crude TPA crystal under the indicated conditions of the experiment is recovered unchanged in the dispersant.

It is to be assumed that the TPAA content of the TPA circulated in cycle 1, 2, 3, 4 is lower than the TPAA content in the TPA separated in the separating stage 16. In other words, during the course of the two-stage cooling process, the TPAA initially dissolved in the hot acetic acid (206°–210° C.) is partially recrystallized on the solid TPA particles.

EXAMPLES ACCORDING TO THE INVENTION

EXAMPLE 1

As in Comparative Example 2, a dispersion is produced in the agitated vessel 5 made up of TPA having an average particle size of 80μ and acetic acid in a weight ratio of 1:3. After 300 l. of this dispersion has been introduced into the cycle 1, 2, 3, 4, the medium is recirculated by means of the inclined-disk grinding pump 4 operating at 2,000 r.p.m., corresponding to a conveying power of 11,000 l./h. At the same time, the dispersion is heated in 3 to 195°–200° C. thus obtaining a pressure of 10 bar. After the dispersion, heated to 195°–200° C., has been circulated for about 120 minutes, 150 kg. of suspension, corresponding to 37.5 kg. of TPA and 112.5 kg. of acetic acid is continuously introduced per hour from agitator 5 via pump 6 into the cycle 1, 2, 3, 4, and in parallel thereto 500 normal liters of air [liters of air under normal conditions] is introduced per hour into the cycle via pipe connection 7. In the waste gas 1c, exiting above the cooler 1, 5–6% by volume of oxygen is measured.

Under the indicated conditions, the following temperatures are obtained in the system: cooler 1, below the feed of the fresh dispersion: 192° C.; dissolving zone, above heat exchanger 3: 196° C. By way of the pneumatically operated conical-seat valve 8, the suspension circulated in the cycle 1, 2, 3, 4 and having an average particle size of 5–10μ is continuously transferred into the two-stage evaporative crystallization stage 10, 11. In the first cooling stage (agitator 10), a temperature of 150° C. is obtained under a pressure of 2–3 bar, the residence time of the suspension in this cooling stage being about 1–2 hours. In the second cooling stage, a temperature of 50° C. is maintained under a reduced pressure of about 80 millibar. The residence time in this cooling stage is 2–3 hours. The cooled suspension is then conducted via pump 15 into the separating stage 16, the thus-separated moist TPA is washed with acetic acid in a weight ratio of 1:0.6, and dried.

TPAA in dried TPA:
640-670-690-600 p.p.m. (average: 650 p.p.m.)

TPAA in the liquid discharge from the separating stage:
≦30 p.p.m. (=0.003% = lower detection limit).

In case the crude TPA stemming from the oxidation stage has been prewashed with acetic acid, an oxidation catalyst is advantageously added to the fresh dispersion in the agitated vessel 5, in order to accelerate the oxidation, for example per hour 11.2 g. of cobalt acetate, 11.5 g. of potassium bromide, and 0.75 g. of manganese acetate. Under these conditions, with otherwise unchanged experimental parameters, the same result is obtained as in Example 1.

If, instead of the inclined-disk grinding pump, a trigonal toothed rotary mill of the same efficiency is utilized, then a TPA having a content of TPAA of 580 p.p.m. is obtained under otherwise identical conditions.

EXAMPLE 2

Example 1 is repeated, but under otherwise identical conditions the conveying power of the inclined-disk grinding pump 4 is increased to 13,000 l./h. (=2,500 r.p.m.) while comminuting the TPA particles to an average diameter of about 5μ. Furthermore, the temperatures are increased as follows: cooler 1, below the feed of the fresh dispersion: 196° C.; dissolving zone, above heater 3: 200° C. The pressure in the system is 11 bar. The TPA, isolated analogously to the procedure of Example 1, has the following analytical data:

TPAA in dried TPA:
470-540-520-480 p.p.m. (average = 500 p.p.m.)

TPAA in the liquid discharge from the separating stage:

≦30 p.p.m. (=0.003%=lower detection limit).

If the air, rather than being introduced via pipe 7, is fed through a quill shaft to the inclined-disk grinding pump directly into the grinding zone, then the oxygen absorption is raised and only up to 4% oxygen is measured in the waste gas.

EXAMPLE 3

Starting material: TPA having 2.42% TPAA

| Suspension: Weight ratio | |
|---|---|
| TPA : HAc | = 1 : 3 |
| Feed/Hour | = 150 kg. |
| Air/Hour | = 500 l. |
| O₂ in Waste Gas | = 6% |
| Operating conditions, temperatures: | |
| Cooler (1) | = 194° C. |
| Dissolving Zone (after 3) | = 199° C. |
| Pressure | = 11 bar |
| Inclined-Disk Grinding Pump | = 2,500 r.p.m. |

In the stationary condition, a temperature of 150° C. is obtained in the first cooling stage (agitator 10) under a pressure of 2–3 bar, and correspondingly in the second cooling stage (agitator 11), under a reduced pressure of 80 millibar, a temperature of 50° C. is obtained. In contrast to the mode of operation in Examples 1 and 2, a total of 100 l. of acetic acid per hour is reintroduced into the cycle 1, 2, 3, 4 in the two-stage evaporative cooling process via pumps 13 and 13a from the receivers 12 and 12a by way of the conduits 14 and 14a, and thus the soluble amount of TPA is almost doubled as compared with the preceding examples.

Discharge:

TPAA in dried TPA:

200-230-240-200 p.p.m. (average=220 p.p.m.)

TPAA in the liquid discharge from the separating stage:

≦30 p.p.m. (=0.003%=lower detection limit)

In other words, in this mode of operation, more than 99% of the TPAA originally contained in the crude TPA (=24,200 p.p.m.) is removed.

We claim:

1. Process for the purification of crude terephthalic acid having about 0.5 to 5 percent by weight of terephthalaldehydic acid therein comprising:
    (a) introducing and circulating a dispersion of particles of said terephthalic acid in an acetic acid dispersant continuously through a cycle comprising a comminuting pump, a heater and a cooler, said cooler functioning as a crystallizer;
    (b) adding fresh dispersion continuously to said cycle while simultaneously removing a corresponding amount of treated dispersion from said cycle;
    (c) subjecting said circulating dispersion, prior to entering the heater to a particle comminution of said particles to about 50–90% of their diameters and exposing said circulating dispersion upstream of or in the heater to an oxygen-containing gas; and
    (d) recovering terephthalic acid product from said treated dispersion, said product having about 0.01 to 0.07 percent by weight of terephthalaldehydic acid therein,
    wherein the average diameter of said particles introduced in step (a) is about 10 to 150 microns and said comminuted particles of step (c) is about 5 to 10 microns.

2. The process of claim 1, wherein an oxidation catalyst is added to the dispersion.

3. The process of claim 1 wherein the temperature range of the dispersion in the cycle is about 180–210° C.

4. Process of claim 3, wherein the temperature difference between the heater and the cooler is 2–6° C.

5. The process of claim 4, wherein said treated dispersion removed from step (b) is processed to remove said acetic acid and said acetic acid is recycled to step (a).

6. The process of claim 1, wherein a temperature range of about 195° C. to 210° C. is maintained in said heater and a temperature range of about 180° C. to 195° C. is maintained in said cooler.

7. The process of claim 1, wherein said oxygen-containing gas is introduced in said heater.

8. The process of claim 1, wherein said oxygen-containing gas is introduced in said comminuting pump.

9. The process of claim 1, wherein said terephthalic acid of step (a) is dispersed in said acetic acid in a weight ratio of terephthalic acid to acetic acid of 5:95 to 60:40.

10. The process of claim 9, wherein said crude terephthalic acid is introduced to step (a) at a rate of about 15 to 150 kilograms per hour and the cycle is circulated at a rate of about 1500 to 30,000 liters per hour.

11. The process of claim 10, wherein the average number of cycles carried out through said comminuting pump, said heater and said cooler is about 5 to 100.

12. The process of claim 11, wherein said oxygen-containing gas is air and said air is introduced at the rate of about 150 to 1500 liters per hour and the percent by volume of oxygen in the waste gas from said cooler is about 1 to 4.

13. The process of claim 12, wherein acetic acid removed with said treated dispersion of step (b) comprises about 50 to 500 percent by weight of said dispersant introduced in step (a) and is separated and recycled at the rate of about 50 to 500 liters per hour.

* * * * *